United States Patent
Steiner

(10) Patent No.: US 10,806,242 B2
(45) Date of Patent: *Oct. 20, 2020

(54) BRUSH FOR LICE OR OTHER PARASITIC INSECTS

(71) Applicant: Patricia E. Steiner, Lomita, CA (US)

(72) Inventor: Patricia E. Steiner, Lomita, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/260,521

(22) Filed: Jan. 29, 2019

(65) Prior Publication Data
US 2019/0246782 A1    Aug. 15, 2019

Related U.S. Application Data

(63) Continuation of application No. 15/340,566, filed on Nov. 1, 2016, now Pat. No. 10,194,738.

(60) Provisional application No. 62/250,410, filed on Nov. 3, 2015.

(51) Int. Cl.
    *A46B 9/02*    (2006.01)
    *A46D 1/00*    (2006.01)
    *A61B 17/50*   (2006.01)

(52) U.S. Cl.
    CPC .............. *A46B 9/023* (2013.01); *A46D 1/02* (2013.01); *A46D 1/0261* (2013.01); *A46B 2200/104* (2013.01); *A46D 1/0284* (2013.01); *A61B 2017/505* (2013.01)

(58) Field of Classification Search
    CPC ...... A46D 1/02; A46D 1/0261; A46D 1/0253; A46D 1/0276; A46D 1/0284; A46B 2200/104; A46B 9/023; A45D 24/30; A61B 2017/505

USPC ...................... 132/125; 15/159.1–160, 207.2
See application file for complete search history.

(56) References Cited

U.S. PATENT DOCUMENTS

| | | | |
|---|---|---|---|
| D188,712 S | 8/1960 | Baumgartner |
| 3,575,183 A | 4/1971 | Tanner, Sr. |
| 5,327,611 A | 7/1994 | Balster et al. |
| 5,873,374 A | 2/1999 | Sanz |
| 8,967,157 B2 | 3/2015 | Steiner |
| 9,326,579 B2 | 5/2016 | Steiner |
| 10,194,738 B2 | 2/2019 | Steiner |
| 2002/0078972 A1 | 6/2002 | Levandovsky |
| 2009/0211047 A1 | 8/2009 | Chen |
| 2015/0024080 A1 | 1/2015 | Jacob et al. |
| 2016/0242525 A1 | 8/2016 | Steiner |

FOREIGN PATENT DOCUMENTS

| | | |
|---|---|---|
| EP | 2366307 A1 | 9/2011 |
| GB | 2440115 A | 1/2008 |

*Primary Examiner* — Laura C Guidotti
(74) *Attorney, Agent, or Firm* — Knobbe Martens Olson & Bear, LLP

(57) ABSTRACT

A lice brush includes a body that supports a plurality of bristles. The body also includes a handle. One or more of the plurality of bristles is configured for use in brushing a user's hair for lice. In particular, one or more of the bristles includes recesses, grooves, indentations, notches, pits or similar inwardly-extending spaces configured to facilitate removal of lice as the bristles pass through the hair. Multiple bristles can be provided in a bristle unit and multiple bristle units can be employed in a bristle assembly of the brush.

22 Claims, 10 Drawing Sheets

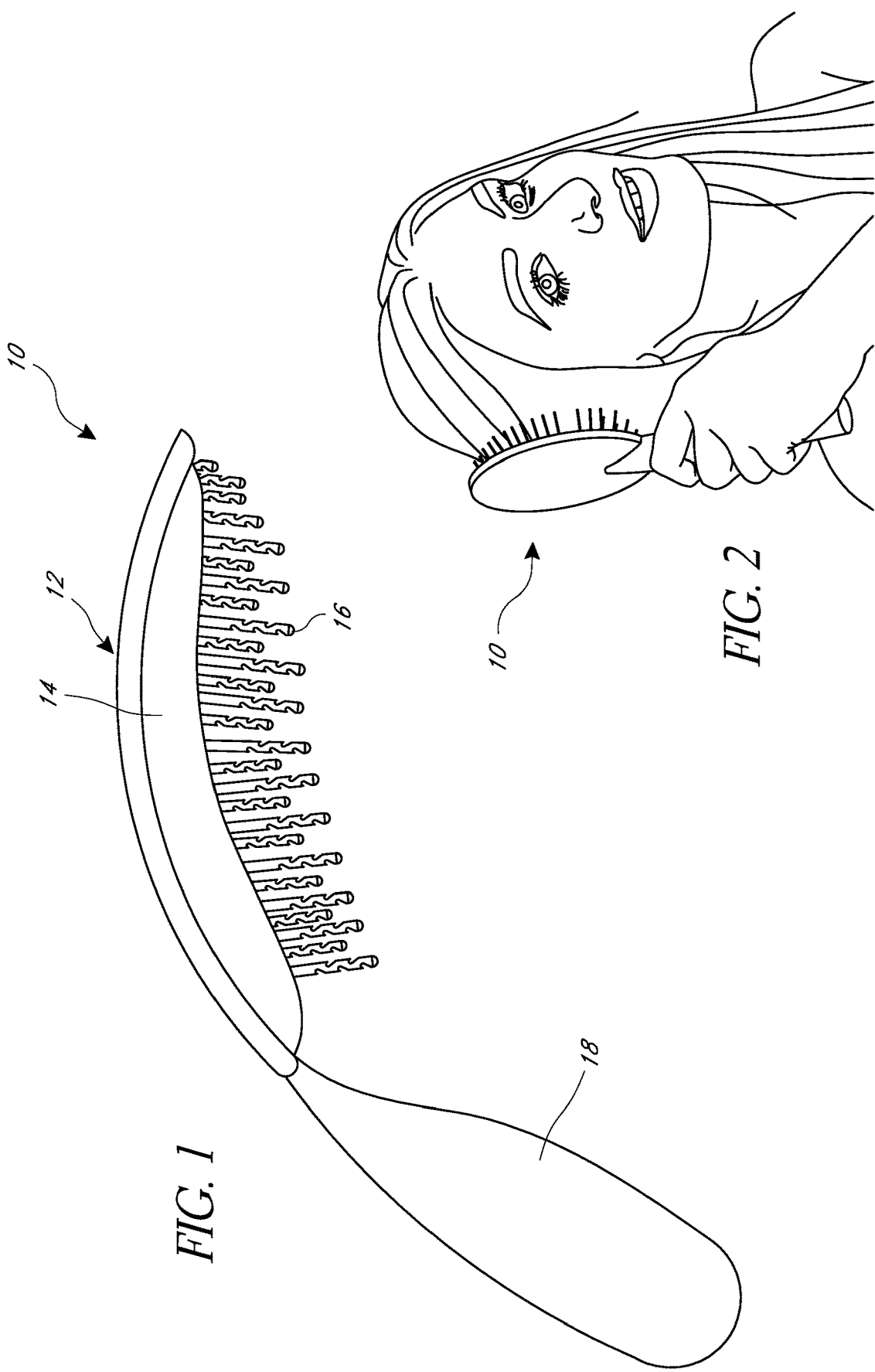

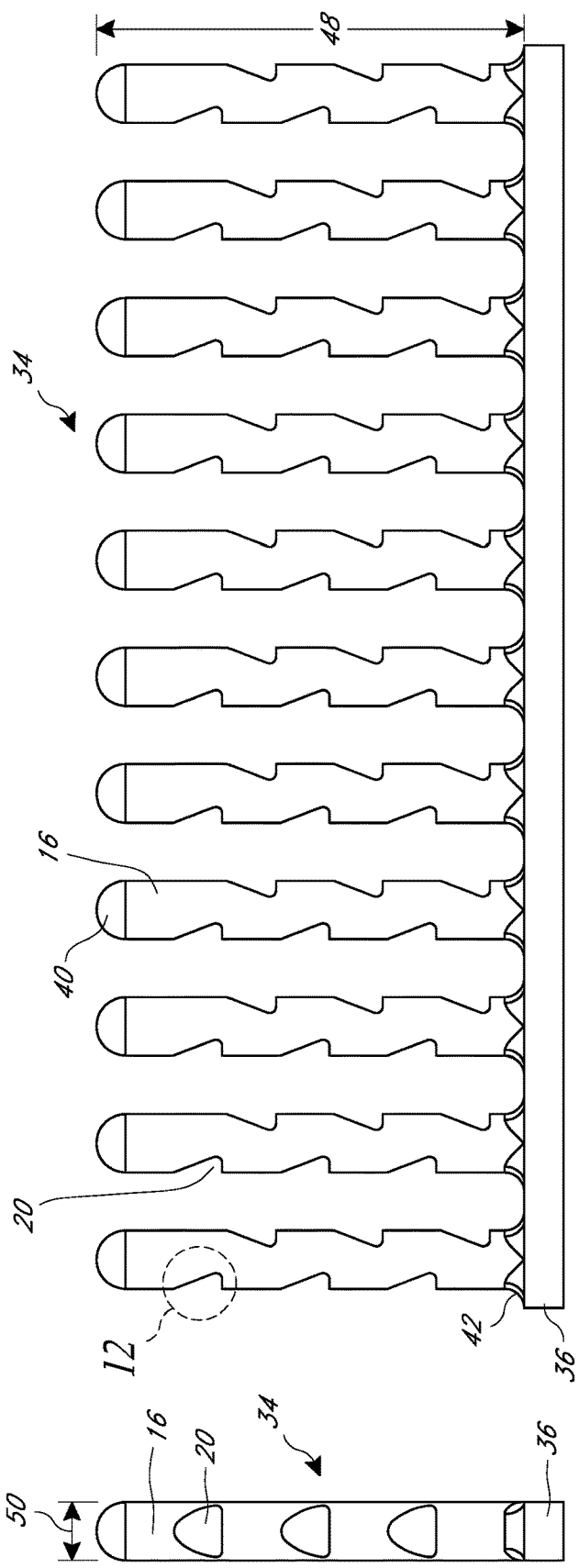
FIG. 10
FIG. 9
FIG. 11

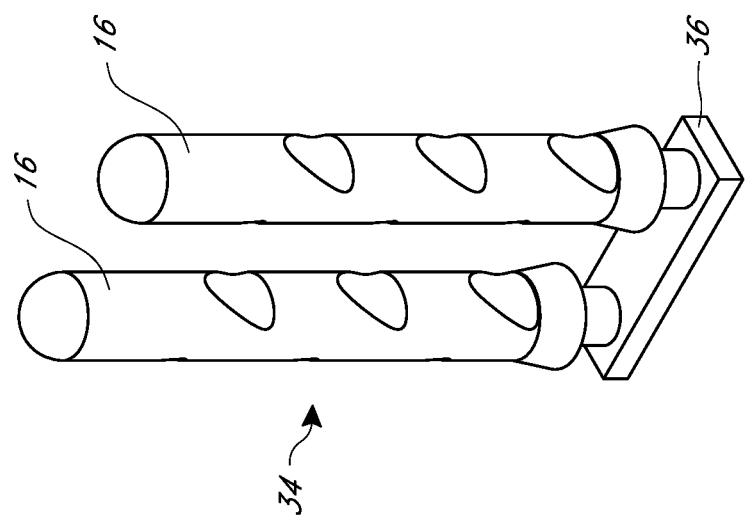
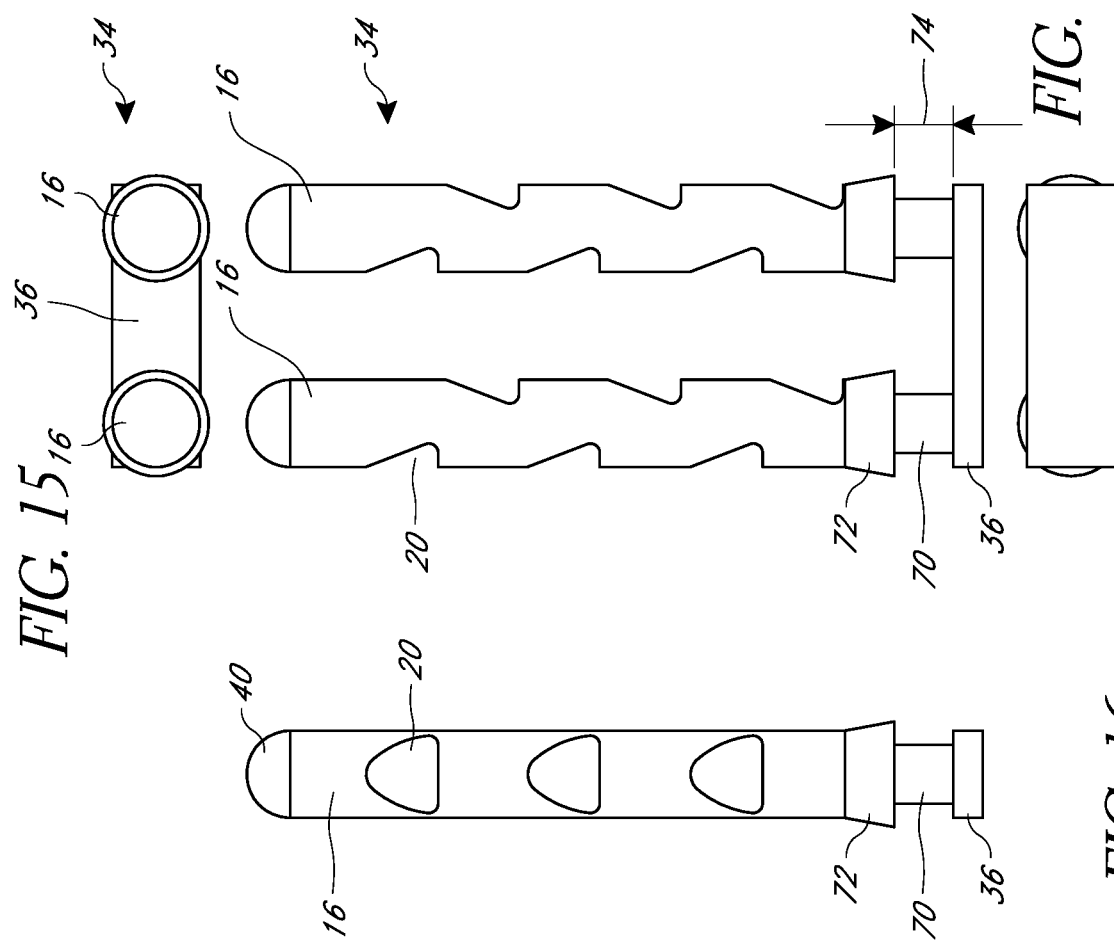

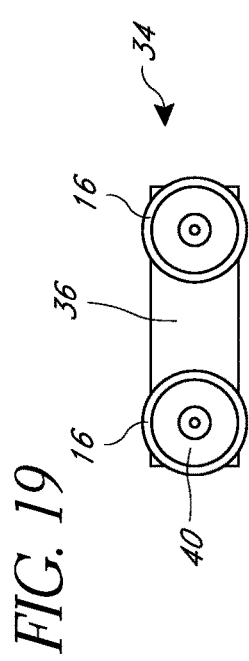
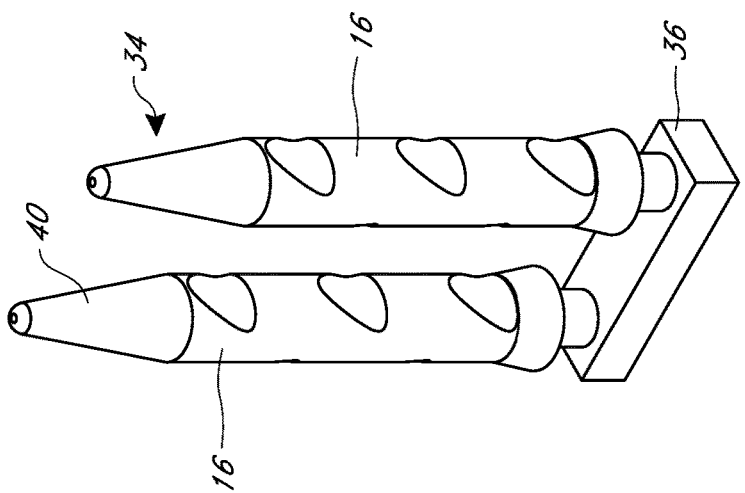
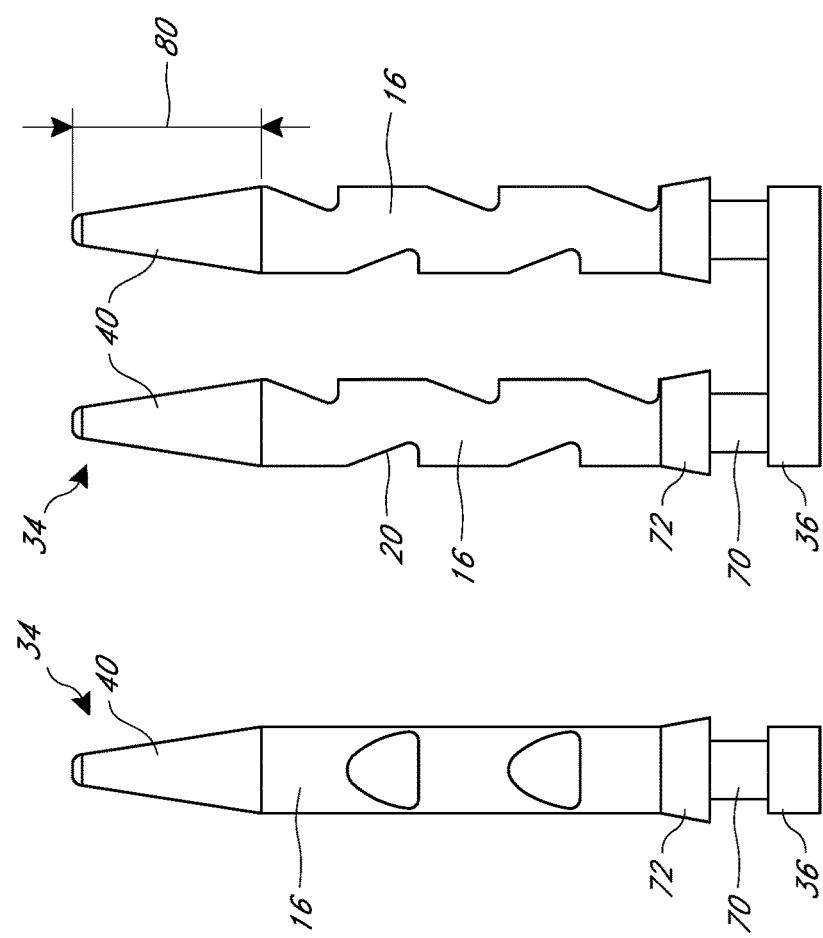
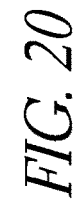

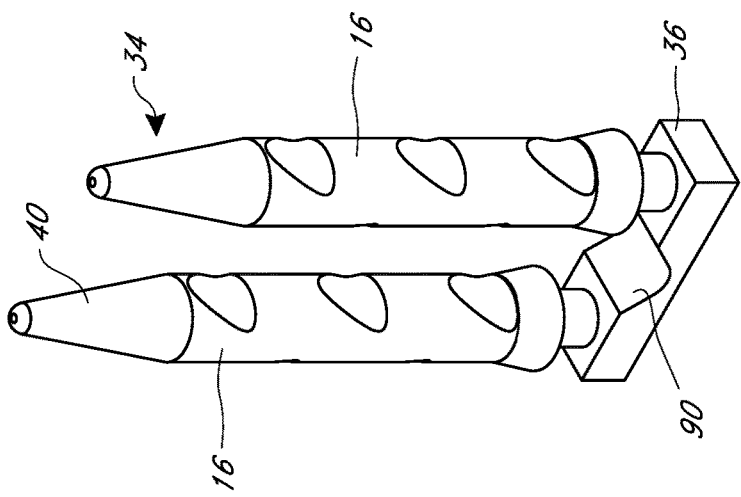
FIG. 21
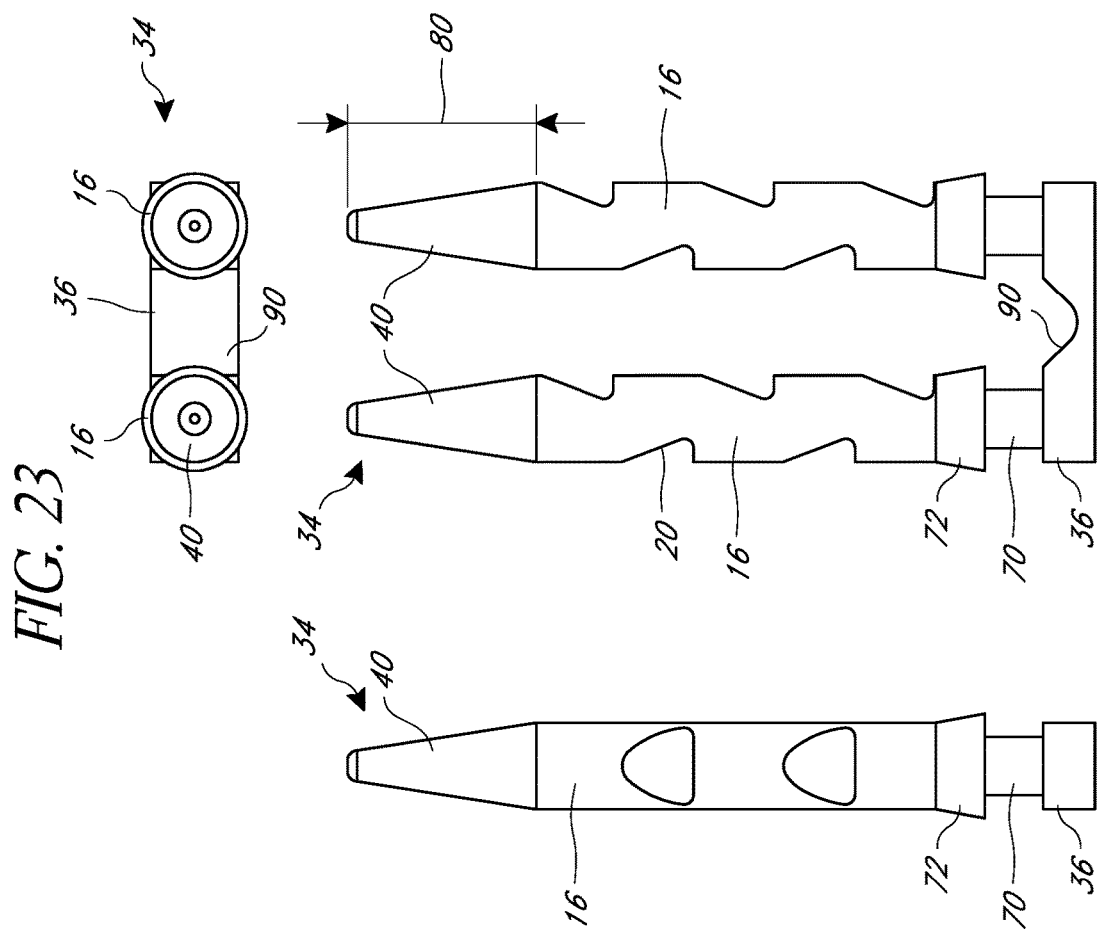
FIG. 23
FIG. 22
FIG. 24

BRUSH FOR LICE OR OTHER PARASITIC INSECTS

INCORPORATION BY REFERENCE TO RELATED APPLICATIONS

Any and all applications identified in a priority claim in the Application Data Sheet, or any correction thereto, are hereby incorporated by reference herein and made a part of the present disclosure.

BACKGROUND

Field

The disclosure generally relates to removal or treatment products for parasitic insects, such as lice or fleas. In particular, the disclosure relates to lice or flea brushes or combs.

Description of Related Art

Lice has become an epidemic worldwide and so far, there is no solution in sight as more and more parents are discovering the resistance to many lice treatment shampoos or other topical products. For years, removing lice and nits from hair has been a tedious, ongoing, old fashioned process that can take hours and hours. In this day and age, time to do this is a rare commodity. There are plenty of lice combs, lice zapping gadgets, lice repellants etc. that claim to remove lice and nits. Although many will remove lice, most are not sufficient to remove nits or they can take hours to remove the parasite from heads. Furthermore, when children have lice, adults living in that household will likely be infected too. If nits are not removed, within 2-3 weeks or so, the child and the rest of the family are again infested with lice because the nits hatch and lice spreads from head to head again. Lice are most often recycled because the child or other family members have been treated inadequately. The situation is similar for fleas.

SUMMARY

The systems, methods and devices described herein have innovative aspects, no single one of which is indispensable or solely responsible for their desirable attributes. Without limiting the scope of the claims, some of the advantageous features will now be summarized.

An embodiment involves a lice brush having a body, which includes a handle, and a plurality of bristles. Each of the plurality of bristles is configured for use in brushing a user's hair for lice. In particular, each of the bristles has recesses, grooves, indentations, notches, pits or similar inwardly-extending spaces configured to catch lice as the bristles pass through the hair.

In some configurations, the plurality of bristles is arranged in both rows and columns.

In some configurations, a portion of the body of the brush that contains the plurality of bristles has a curved shape. In some such configurations, the portion of the body is curved in width and length directions.

In some configurations, the body of the brush comprises a handle and the handle is curved.

An embodiment involves a lice brush having a body and a plurality of bristles. The body includes a main body portion and a handle. The plurality of bristles is supported by the main body portion. The plurality of bristles is arranged in a plurality of rows spaced apart from one another along a length or width direction of the main body. Each of the plurality of bristles comprises a plurality of indentations spaced apart from one another along a length direction of the bristle.

In some configurations, the main body portion of the brush has a curved shape.

In some configurations, the main body portion is curved in both the width direction and the length direction.

In some configurations, the handle is curved.

In some configurations, a first portion of the plurality of indentations is located on a first side of the bristle and a second portion of the plurality of indentations is located on a second side of the bristle opposite the first side.

In some configurations, the first portion of the plurality of indentations is offset along the length direction of the bristle relative to the second portion of the plurality of indentations.

In some configurations, the offset is equal to a length of the indentation in the length direction of the bristle.

In some configurations, a spacing between the first portion or the second portion of the plurality of indentations is equal to the length of the indentation in the length direction of the bristle.

In some configurations, each of the plurality of indentations is defined by an oblique wall and a radial wall relative to the length direction of the bristle.

In some configurations, a rounded transition is located between the oblique wall and the radial wall.

In some configurations, a length of the indentation is 2.5 millimeters and a depth of the indentation is 0.8 millimeters.

In some configurations, each of the plurality of bristles has a rounded tip.

In some configurations, each of the plurality of bristles has a tapered tip.

In some configurations, a first portion of the plurality of bristles is interconnected by a first base and a second portion of the plurality of bristles is interconnected by a second base.

In some configurations, a rounded transition between the first base and each of the first portion of the plurality of bristles and between the second base and each of the second portion of the plurality of bristles.

In some configurations, a reduced-diameter shaft portion is located between the first base and each of the first portion of the plurality of bristles and between the second base and each of the second portion of the plurality of bristles.

In some configurations, a recess is formed in the first base or the second base between adjacent ones of the first portion or the second portion of the plurality of bristles.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 1 is a perspective view of a brush for parasitic insects having certain features, aspects and advantages of a preferred embodiment.

FIG. 2 is a view of a user using the brush of FIG. 1.

FIG. 9 is a side view of the bristle unit of FIG. 8.

FIG. 10 is a top view of the bristle unit of FIG. 8.

FIG. 11 is an end view of the bristle unit of FIG. 8.

FIG. 13 is a perspective view of another bristle unit.

FIG. 14 is a side view of the bristle unit of FIG. 13.

FIG. 15 is a top view of the bristle unit of FIG. 13.

FIG. 16 is an end view of the bristle unit of FIG. 13.

FIG. 17 is a perspective view of yet another bristle unit.

FIG. 18 is a side view of the bristle unit of FIG. 17.

FIG. 19 is a top view of the bristle unit of FIG. 17.

FIG. 20 is an end view of the bristle unit of FIG. 17.

FIG. 21 is a perspective view of a modification of the bristle unit of FIG. 17.

FIG. 22 is a side view of the bristle unit of FIG. 21.

FIG. 23 is a top view of the bristle unit of FIG. 21.

FIG. 24 is an end view of the bristle unit of FIG. 21.

DETAILED DESCRIPTION

Figure 5:
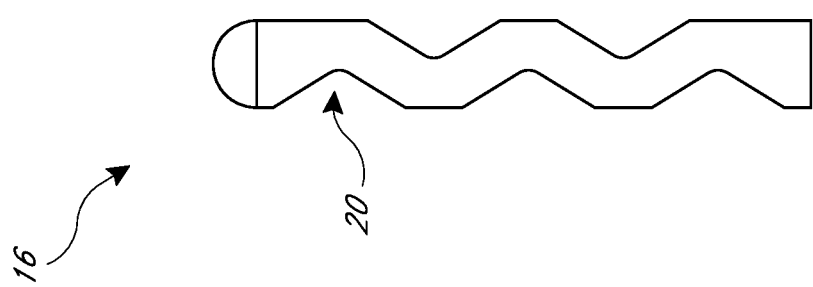
FIG. 5 is an enlarged view of another example of a bristle of the brush of FIG. 1.

An aspect of the present invention involves the realization by the present inventor that brushing hair on a regular basis can remove lice from hair and can help inhibit or prevent lice from laying eggs in a person's hair. Preferably, the brush includes bristles that are configured to assist in removing lice from the hair. One or more (including all) of the bristles can include lice-removing features, which in some configurations can be in the form of grooves or recesses formed in the outer surface of shaft portion of the bristle. In some configurations, multiple grooves, recesses or other lice-removing features can be provided and spaced from one another along a length and/or around a circumference of the bristle.

Through head to head contact, a louse can makes its way into a child's head and if the louse is a fertilized female, it will start laying eggs, usually about 24 hours later. Hair that is not brushed makes the perfect home for lice. They are undisturbed to get on with their business of re-producing. Giving the hair a good brushing disturbs or removes the lice and interrupts that reproduction cycle. Regular brushing can remove lice from hair. These days, families are so busy that children can go days without a good hair brushing. In addition, if a child is sensitive to having his or her hair brushed, that child can go an extended period without a good hair brushing.

Lice hold onto hair with their 'claws' at the end of their feet, swinging from hair to hair. Passing the lice brush through hair can catch them and stop them from laying eggs. If a good hair brushing is done it can stop lice by making it a very unpleasant place to lay eggs. Hair brushing can be a good repellant, as opposed to the most common things, such as Tea Tree Oil, Peppermint sprays, etc. which don't seem to be slowing lice down. If we attack their home with good hair brushing habits, they won't get a chance to lay eggs.

Brushing the hair, especially with a brush configured to remove lice, can be a form of prevention of lice infestation. Instead of waiting until their kids itch, using a brush configured to remove lice can provide a preventative measure to be taken. It is often too late once the eggs are hatching and the lice offspring are laying their own eggs to fully address the lice infestation with brushing alone. However, with a good hair brushing, that little creature right there, in that hair, can actually be brushed out. If the lice have laid eggs, the brush likely won't be effective because eggs are cemented to the hair. However, using a lice comb will remove the eggs and because of the brushing, there won't be as many. Thus, an aspect of an embodiment can involve a method of lice (or other parasitic insect) infestation comprising regular brushing with a brush configured for lice removal and, in some cases, use of a lice comb to remove nits and/or eggs.

One or more embodiments of the present brush or portions thereof are designed to facilitate removal of lice or other parasitic or similar insects, which is advantageous because prevention or early removal is a key to lice control. Because the preferred embodiments are easy to use as an 'every day' lice brush, it will encourage brushing of hair on a regular basis, so that an early removal of lice can be facilitated before it gets to an infestation. The lice brush can be easily swiped through the hair on a regular basis, after bathing, before school, etc. The easy to use designs of the preferred embodiments will encourage brushing and, thus, removal of live lice before they can infest the hair. Because lice is spread head to head, especially in schools, camps, pre-schools, etc., routine brushing during the peak outbreaks of lice infestations, such as summertime, summer camps, the weeks following back to school, etc. is encouraged as part of a lice prevention routine to pick up any lice that may have gotten into the hair. Prevention of infestation by brushing is a big part of stopping the recycling of lice and as more and more children and families are dealing with lice, the 'prevention brushing' will be beneficial, especially if the brush is quick, comfortable and easy to use. There is also the removal of lice on an infested child. The brush is easy and quicker to use as opposed to the standard method, which is to painstakingly remove one nit at a time or section off the hair inch by inch.

Configurations of the lice, flea or other parasitic insect brush 10 can include one or more of the following features, many of which are illustrated in the accompanying drawings. With reference to FIGS. 1-5, the brush 10 has a body 12, which includes a first portion or main body portion 14 that supports a plurality of tines or bristles 16 and a second portion or handle 18 that extends from the first portion 14. The main body portion 14 preferably is curved in one or both of the width and length directions. In some configurations, the handle 18 can be curved and can have a similar curvature as the main body portion 14. As is typical of a brush, the bristles 16 can be arranged in multiple rows or columns such that multiple bristles 16 are provided in both a lengthwise direction of the brush 10 and a widthwise direction of the brush 10.

Figure 4:
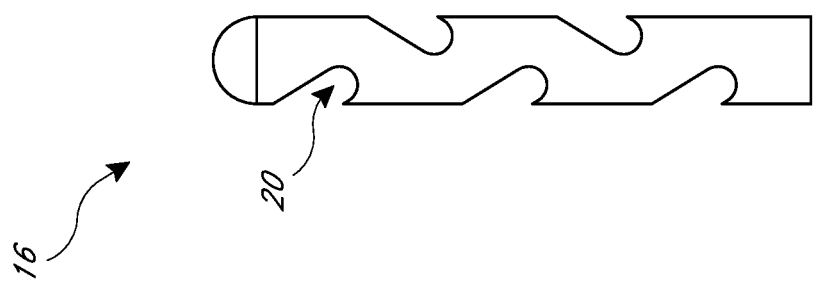
FIG. 4 is an enlarged view of an example of a bristle of the brush of FIG. 1.
Figure 3:
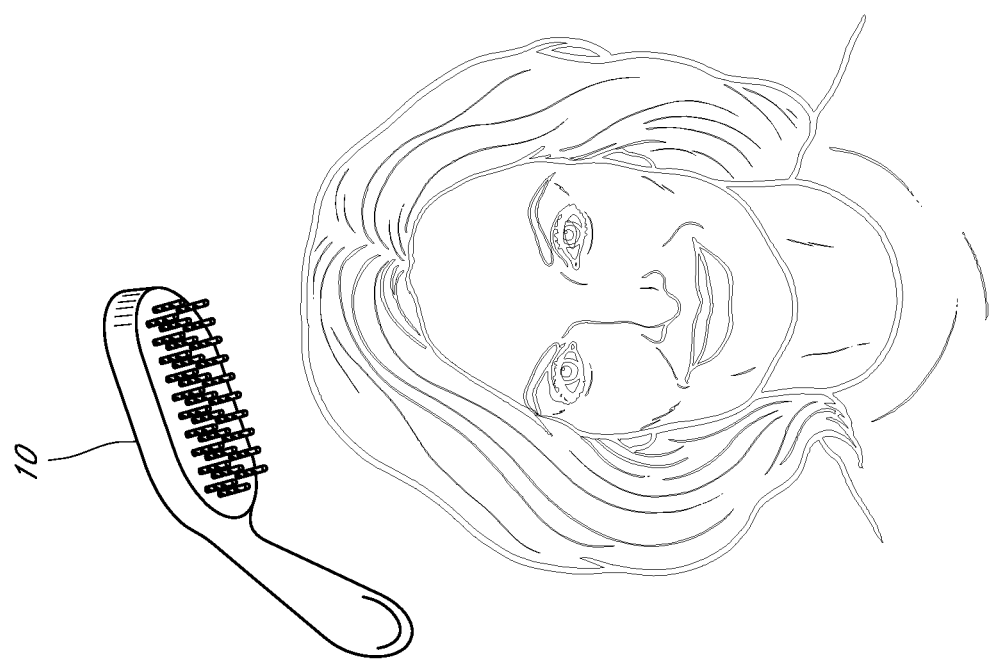
FIG. 3 is a perspective view of the brush of FIG. 1 adjacent the head of a user.

With reference to FIGS. 4 and 5, each bristle 16 of the lice brush 10 has one or more interruptions, protrusions or indentations 20 (any of which can be referred to as indentations herein for the sake of convenience) that are configured to catch lice as the bristle 16 passes through the hair strands. The indentations 20 can be of any suitable arrangement, such as recesses, grooves, ridges, indentations, notches, pits or similar inwardly-extending spaces configured to catch lice as the bristles pass through the hair. The inwardly-extending spaces can extend inwardly from an outer surface of a main portion of the shaft of the bristle 16 or can extend inwardly from a protrusion or protruding portion of the bristle 16. Thus, in some configurations, an inwardly-extending space can be defined between a pair of spaced-apart protrusions.

Preferably, multiple indentations 20 are provided on each bristle 16. In some configurations, the open ends or portions of the indentations 20 face radially relative to a length of the bristle 16. In some configurations, the open end or portions of the indentations 20 face or are angled toward a free end of the bristle 16. That is, a wall or walls that define the indentation 20 can be angled relative to a longitudinal axis of the bristle 16. However, in other arrangements, the opening of the indentations 20 can face toward the main body 14 end of the bristle 16. The indentations 20 can be the same within a bristle 16 or the brush 10 or can vary within a bristle 16 or the brush 10. That is, the indentations 20 can be different between the plurality of bristles 16 of the brush 10. The shape of the indentations 20 can vary. For example, with reference to FIG. 4, the indentations 20 can be rounded. With reference to FIG. 5, the indentations 20 can have linear walls that result in an angular shape (e.g., triangular). Other suitable shapes can also be used. Preferably, the indentations 20 can be sized or shaped to allow a single hair or a small number of hairs to occupy the indentation 20 as the bristle 16 moves along the hair such that the edges of the indentations 20 remove lice from the hair strand(s).

Figure 6:
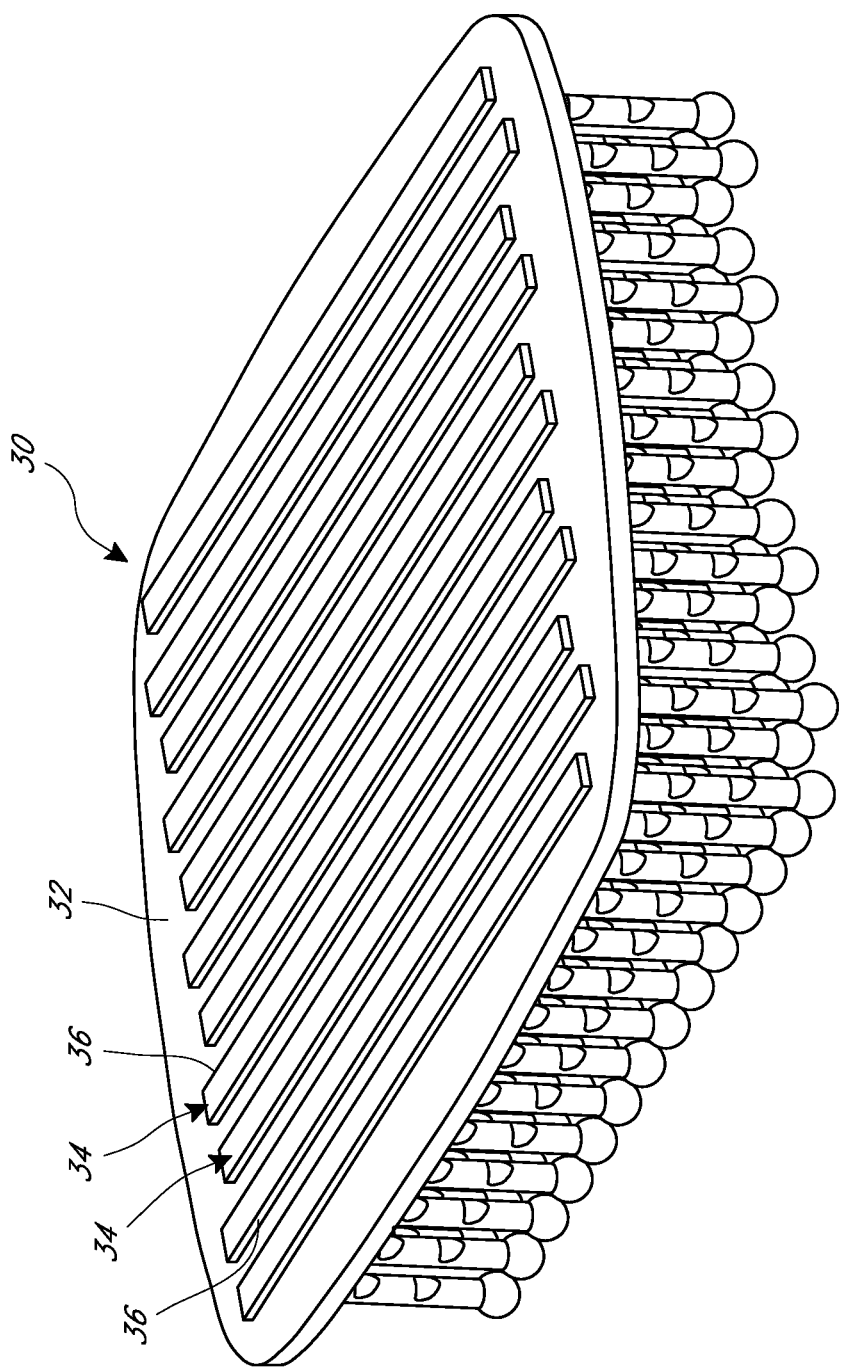
FIG. 6 is a perspective view of a bristle assembly having a base and a plurality of bristle units.

FIG. 6 is a perspective view of a bristle assembly 30 having a base 32 and a plurality of bristle units 34. The base 32 can support the bristle units 34 in a desired position relative to one another. The base 32 can allow for efficient assembly of the brush 10 by permitting the bristle units 34 to be assembled to the base 32 to create a sub-assembly, which can then be secured to the main body portion 14 of the brush 10 by any suitable arrangement. In the illustrated arrangement, the base 32 is in the form of a flat plate and the bristle units 34 are positioned substantially parallel to one another to define separate rows or columns of bristles 16. The bristle units 34 can extend in a lengthwise or a widthwise direction of the brush 10.

Each bristle unit 34 includes a plurality of bristles 16, which can be of any suitable arrangement, such as any individual one or combination of those described herein. The bristles 16 of each bristle unit 34 are attached to a base 36, which interconnects the bristles 16. In some configurations, the bristles 16 and the base 36 are formed as a unitary structure, such as by an injection molding process, for example. The bristle unit 34 can include any suitable number of bristles 16, which can depend on the size of the brush 10, for example. In the illustrated arrangement, each row or column of bristles 16 includes only a single base 36; however, in other arrangements multiple rows or columns of bristles 16 can be coupled to a base 36.

Figure 7:
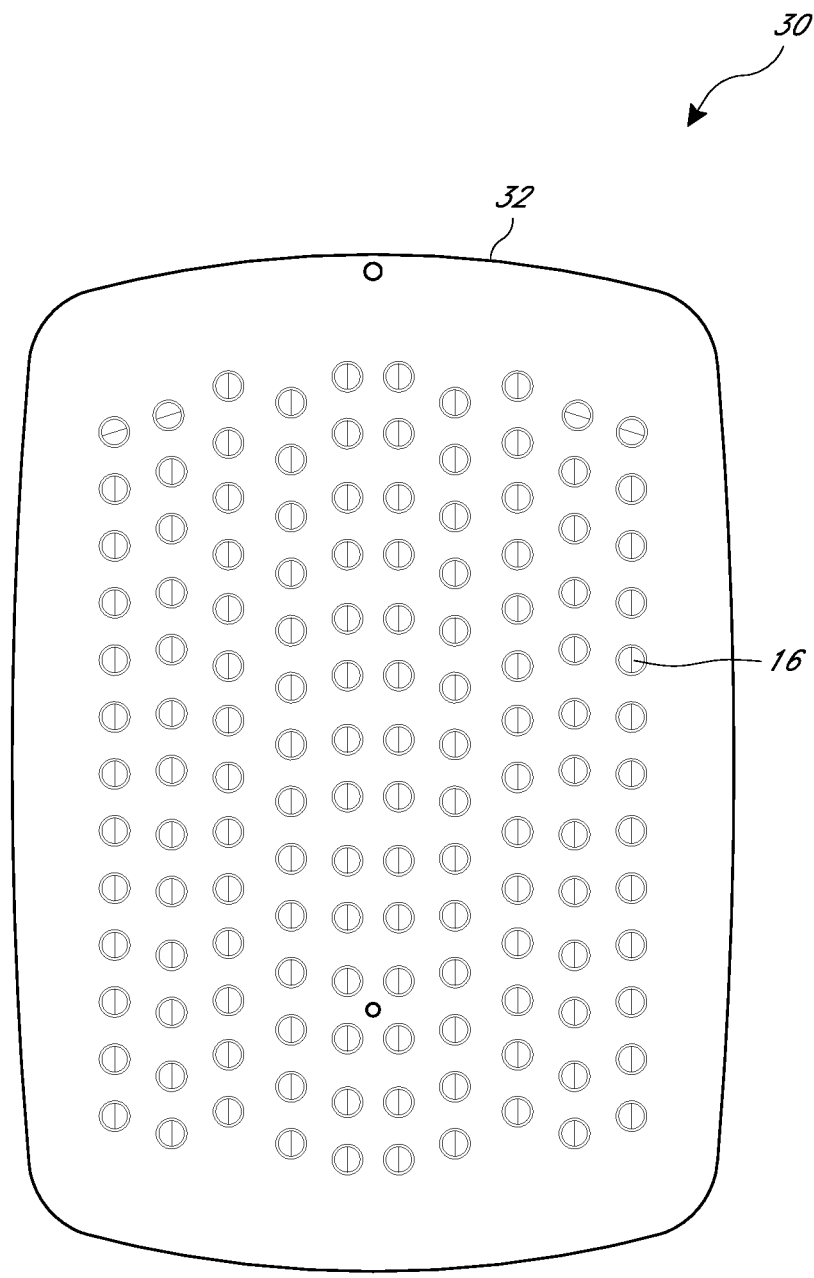
FIG. 7 is a front view of the bristle assembly of FIG. 6.
Figure 8:
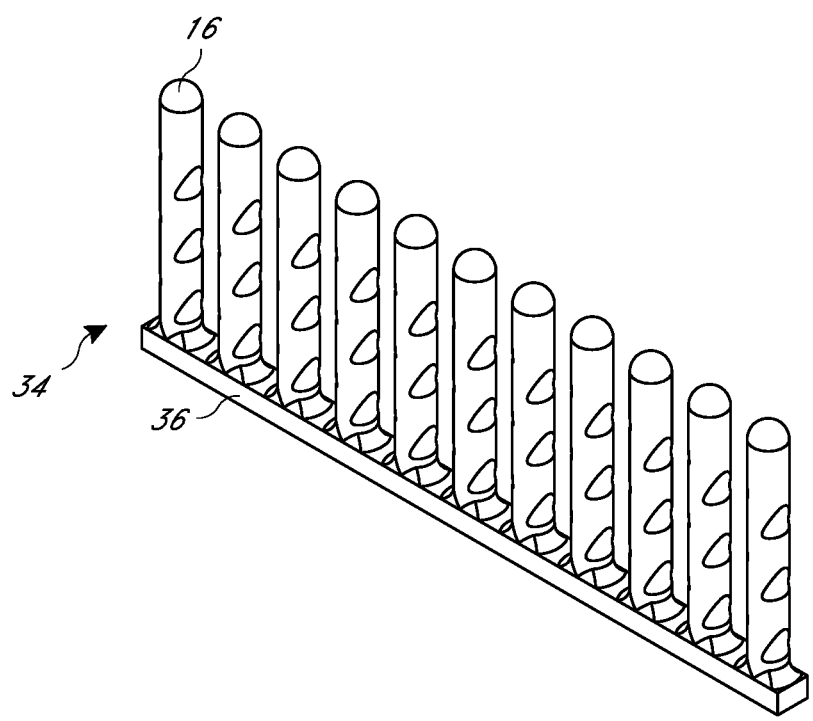
FIG. 8 is a perspective view of a bristle unit of the bristle assembly of FIG. 7.

FIG. 7 illustrates an example of a layout of the bristles 16 on the base 32 of the bristle assembly 30. In the illustrated arrangement, at least a portion of adjacent columns (based on the vertical orientation in FIG. 7; however, could also be referred to more generically as "rows") are offset from one another such that the individual bristles 16 of adjacent columns are not horizontally aligned with one another. However, in some configurations, at least a portion of adjacent columns are aligned with one another. For example, in the illustrated arrangement, the center two columns are horizontally aligned with one another. However, in other configurations, all of the columns (or rows) could be aligned, all adjacent columns (or rows) could be offset or all of the columns (rows) could be offset.

FIGS. 8-12 illustrate several views of a bristle unit 34 separate from the base 32. The bristle unit 34 includes bristles 16 aligned in a row and attached to a base 36. Each bristle 16 defines a free end opposite a fixed end that is attached to the base 36. In the illustrated arrangement, the free ends define a rounded or hemispherical tip 40, which can provide comfort to a user of the associated brush 10 when the bristles 16 contact the user's skin. In addition, a rounded transition or chamfer 42 is provided between the base 32 and the fixed end of each of the bristles 16. The chamfer 42 can provide support to the bristles 16 to reduce flexing and eliminate sharp edges or transitions to avoid catching the user's hair or to prevent stress risers in the material thereby increasing the useful life of the bristle unit 34 and associated brush 10. The illustrated bristle unit 34 includes eleven bristles 16, however other suitable numbers of bristles 34 can also be provided, such as between two and thirty bristles 16, five and twenty bristles 16 or ten and fifteen bristles 16, including any value or sub-range within these ranges.

The bristles 16, bristle units 34, bristle assembly 30 and associated brush 10 can have any suitable dimensions for the intended use of lice removal or reduction by brushing a user's hair. The dimensions may vary, for example, with the intended user. That is, the brush 10 or any components thereof can be provided in a first size for adult use and a second size for child use, for example and without limitation. In one configuration, each bristle 16 can have a height 48 of between 15-30 mm, 20-25 mm or about 22 mm, or any value or sub-range within these ranges. Each bristle 16 can have a diameter 50 of between 1-5 mm, 2-4 mm or about 3 mm, or any value or sub-range within these ranges. The bristles 16 can be spaced about 4-8 mm, 5-7 mm or about 6 mm on center.

As described herein, each bristle 16 can include one or more indentations 20. In the configuration of FIGS. 8-12, each bristle 16 includes six indentations 20; however, other numbers may be provided depending, for example, on the length of the bristles 16 or the size of the indentations 20. In some configurations, each bristle 16 includes between two-ten indentations 20 or between four-eight indentations 20, including any value or sub-range within these ranges. In the illustrated configuration, the indentations 20 are arranged on opposite sides of the bristle 16. That is, the indentations 20 are diametrically opposed from one another on the bristle 16. The bristle 16 can have the same number of indentations 20 on each side. In some configurations, the indentations 20 can be spaced-apart from one another by the same distance. In some configurations, the indentations 20 on one side of the bristle 16 are offset from the indentations 20 on the other side of the bristle 16 along a longitudinal axis of the bristle 20. Such an arrangement can reduce or prevent weakening of the bristle 16 that could occur if the indentations 20 on opposite sides were aligned. In some configurations, the longitudinal space between indentations 20 can be equal to a length 52 of the indentations 20.

Figure 12:
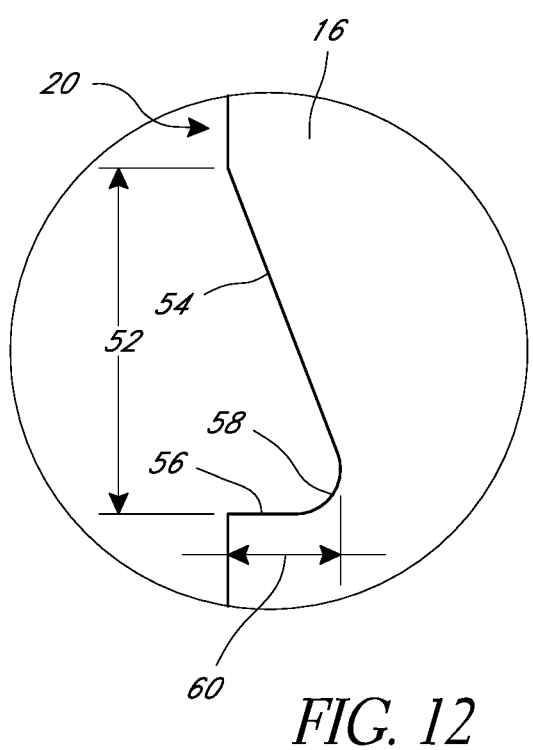
FIG. 12 is an enlarged view of a portion of a bristle of the bristle unit of FIG. 8 illustrating an indentation of the bristle.

With reference to FIG. 12, one or more of the indentations 20 can be defined by a generally L-shaped or V-shaped indented surface. In some configurations, the indentation 20 can include a primarily axially-extending or oblique wall 54 and a primarily radially-extending wall 56. The oblique wall 54 and the radial wall 56 come together at a rounded transition 58. The oblique wall 54 can extend along a substantial portion or an entirety of the length 52 of the indentation 20 and the radial wall 56 can extend along a substantial portion or an entirety of a depth 60 of the indentation 20. The oblique wall 54 can guide hair strands toward the rounded transition 58 and the radial wall 56, which can strip lice off of the hair strands. In the illustrated configuration, the oblique wall 54 is located relatively closer to the tip 40 than the radial wall 56. However, this arrangement could also be reversed.

The size or shape of the indentations 20 can be varied depending on the approximate number of hair strands that are desired to be accommodated in the indentation 20, the type of hair or the size of the target parasitic insect(s). For example, the indentations 20 can have a maximum depth 60 of between about 0.4-1.2 mm, 0.6-1.0 mm or about 0.8 mm. The length 52 of the indentations 20 can be varied in proportion to the depth 60 of the indentations 20. The length 52 could also be varied depending on the desired angle of the oblique wall 54 relative to the longitudinal axis of the bristle 16, with a smaller length 52 resulting in a steeper angle and a larger length 52 resulting in a shallower angle. In some configurations, the length 52 of the indentations 20 can be between about 1-4 mm, 2-3 mm or about 2.5 mm. Other suitable lengths 52 or depths 60 can also be used. The dimensions of the indentations 20 can be consistent within or across bristles 16 or can vary within or across bristles 16.

FIGS. 13-16 illustrate a modification of the bristle unit 34, which can be the same as or substantially similar to the other bristle units 34 disclosed herein except as otherwise noted. Accordingly, the same reference numbers are used to refer to the same, similar or corresponding components. Features or components not specifically described can be the same as or similar to the corresponding features or components of the other bristle units 34 disclosed herein, or can be of another suitable arrangement. The bristles 16 of the bristle unit 34 of FIGS. 13-16 includes a reduced-diameter shaft portion 70 positioned between a tapered shoulder 72 and the base 36. The shaft portion 70 can have a length 74 that is sized to receive the base 32 of the bristle assembly 30 (FIG. 7). The shaft portion 70 can allow the bristle unit 34 to engage the base 32 of the bristle assembly 30 with an interference or snap-fit, for example. In other words, the base 32 can be tightly received between the shoulder 72 and the base 36 of the bristle unit 34.

FIGS. 17-20 illustrate a modification of the bristle unit 34, which can be the same as or substantially similar to the other bristle units 34 disclosed herein except as otherwise noted. Accordingly, the same reference numbers are used to refer to the same, similar or corresponding components. Features or components not specifically described can be the same as or similar to the corresponding features or components of the other bristle units 34 disclosed herein, or can be of another suitable arrangement. The bristles 16 of the bristle unit 34 of FIGS. 17-20 have a tapered tip 40 in contrast to the blunter, hemispherical tip 40 of the prior bristles 16. In some configurations, a terminal end of the tapered tip 40 can be blunt. However, the diameter of the blunt (e.g., hemispherical) end of the tapered tip 40 can be significantly less than the diameter 50 of the shaft of the bristle 16, such as about one-third of the diameter 50 of the shaft of the bristle 16, for example. A length 80 of the tapered tip 40 can define about 20-40% of the overall length of the bristle 16 or can be about 4-8 mm, 5-7 mm or about 6 mm or 6.6 mm.

In addition, the bristles 16 of FIGS. 17-20 have a different number of indentations 20 on opposing sides of the bristle 16. For example, one side has an even number of indentations 20 and the opposite side has an odd number of indentations 20. However, in other arrangements, the number of indentations 20 on opposing sides can both be even or odd, but different from one another. In the illustrated configuration, the bristles 16 each have two indentions 20 on one side and three indentations 20 on the opposite side.

FIGS. 21-24 illustrate a modification of the bristle unit 34 of FIGS. 17-20, which can be the same as or substantially similar to the other bristle units 34 disclosed herein except as otherwise noted. Accordingly, the same reference numbers are used to refer to the same, similar or corresponding components. Features or components not specifically described can be the same as or similar to the corresponding features or components of the other bristle units 34 disclosed herein, or can be of another suitable arrangement. The base 36 of the bristle unit 34 of FIGS. 21-24 comprises a recess or indentation 90 defined by an upper surface or a bristle-side surface and located between the bristles 16. Although only two bristles 16 are illustrated in the bristle unit 34, additional bristles 16 could be provided. A recess 90 can be provided between any number or all of the adjacent pairs of bristles 16 on the bristle unit 34. The recess 90 can be configured to facilitate flex of the base 36 of the bristle unit 34 to allow tilting movement of the bristles 16 relative to one another. Such an arrangement can facilitate assembly to the base 32 of the bristle assembly (FIG. 7) or can provide for flex of the bristles 16 during use of the associated brush 10, which can improve comfort for the user relative to bristle units 34 that do not include any recesses 90 (or fewer recesses 90) in the base 36.

Brushing hair regularly can catch adult lice at the moment they are moving through the hair. If you catch lice early, brushing can stop it in its tracks and if you don't find it the first time, you will eventually brush it out. If a parent, aunt, friend etc. thinks they have been exposed to lice, a good hair brushing, not forgetting to tip the head upside down and brush that way too, can inhibit or prevent an infestation. Lice are always found in hair brushes, so it is preferable to wash the brush after lice is found and not to share brushes between users.

Although described in the context of a lice brush, embodiments of the present disclosure can also find utility in other applications, or be modified for other applications. For example, the brush can be used as a flea brush to extract fleas from the fur of animals, such as dogs or cats, for example. In some cases, it may be desirable to scale up or down some or all portions of the brush to better suit a specific application. For example, a width and/or length of the main body 14 and/or bristles 16 may be scaled down for use with small dogs or cats. The width and/or length of the main body 14 and/or bristles 16 may be scaled up for use with large dogs or other large animals. In general, the size of the handle 18 will be based on the intended user of the brush 10, rather than the intended use. Furthermore, it is contemplated that the features of the bristles 16, bristle units 34 or other portions of the brushes 10 described herein can be applied to a comb, which includes a single row of bristles 16 or multiple rows of bristles 16 that are close to one another such that a teeth/tine/bristle portion of the comb has an elongated, relatively flat shape.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A lice brush, comprising:
   a body comprising a main body portion and a handle;
   a plurality of bristles supported by the main body portion, wherein the plurality of bristles are arranged in a plurality of rows spaced apart from one another along a length or width direction of the main body, wherein a spacing between each of the plurality of bristles in every one of the plurality of rows is equal, and wherein each of the plurality of bristles has a circumference and comprises a plurality of indentations spaced apart from one another along a length direction of the bristle;

wherein a first portion of the plurality of indentations are located on a first side of the bristle and a second portion of the plurality of indentations are located on a second side of the bristle opposite the first side; and wherein the first portion of the plurality of indentations is offset along the length direction of the bristle relative to the second portion of the plurality of indentations such that each of the plurality of indentations extends around only a portion of the circumference of the bristle.

2. The lice brush of claim 1, wherein the main body portion of the brush has a curved shape.

3. The lice brush of claim 2, wherein the main body portion is curved in both the width direction and the length direction.

4. The lice brush of claim 2, wherein the handle is curved.

5. The lice brush of claim 1, wherein the offset is equal to a length of the indentation in the length direction of the bristle.

6. The lice brush of claim 5, wherein a spacing between the first portion or the second portion of the plurality of indentations is equal to the length of the indentation in the length direction of the bristle.

7. The lice brush of claim 6, wherein each of the plurality of indentations is defined by an oblique wall and a radial wall relative to the length direction of the bristle.

8. The lice brush of claim 1, wherein each of the plurality of indentations is defined by an oblique wall and a radial wall relative to the length direction of the bristle.

9. The lice brush of claim 8, further comprising a rounded transition between the oblique wall and the radial wall.

10. The lice brush of claim 8, wherein a length of the indentation is 2.5 millimeters and a depth of the indentation is 0.8 millimeters.

11. The lice brush of claim 8, wherein each of the plurality of bristles has a rounded tip.

12. The lice brush of claim 8, wherein each of the plurality of bristles has a tapered tip.

13. The lice brush of claim 8, wherein the oblique wall extends along a substantial portion or an entirety of a length of the plurality of indentations.

14. The lice brush of claim 8, wherein the radial wall extends along a substantial portion or an entirety of a depth of the plurality of indentations.

15. The lice brush of claim 8, wherein the oblique wall is positioned closer to a tip of the plurality of bristles than the radial wall.

16. The lice brush of claim 1, wherein a first portion of the plurality of bristles is interconnected by a first base and a second portion of the plurality of bristles are interconnected by a second base.

17. The lice brush of claim 16, further comprising a rounded transition between the first base and each of the first portion of the plurality of bristles and between the second base and each of the second portion of the plurality of bristles.

18. The lice brush of claim 16, further comprising a reduced-diameter shaft portion between the first base and each of the first portion of the plurality of bristles and between the second base and each of the second portion of the plurality of bristles.

19. The lice brush of claim 16, further comprising a recess formed in the first base or the second base between adjacent ones of the first portion or the second portion of the plurality of bristles.

20. The lice brush of claim 1, wherein each of the plurality of indentations extends around no more than half of the circumference of the bristle.

21. The lice brush of claim 1, wherein the plurality of indentations are provided along a substantial portion or an entirety of the length direction of the bristle.

22. The lice brush of claim 1, wherein the spacing between each of the plurality of bristles in every one of the plurality of rows is at least 4 mm.

* * * * *